US010724002B2

(12) United States Patent
Slukvin et al.

(10) Patent No.: US 10,724,002 B2
(45) Date of Patent: *Jul. 28, 2020

(54) ERYTHROID CELLS PRODUCING ADULT-TYPE BETA-HEMOGLOBIN GENERATED FROM HUMAN EMBRYONIC STEM CELLS

(71) Applicant: Wisconsin Alumni Research Foundation, Madison, WI (US)

(72) Inventors: Igor I. Slukvin, Verona, WI (US); James A. Thomson, Madison, WI (US); Maksym A. Vodyanyk, Madison, WI (US); Maryna E. Gumenyuk, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/946,101

(22) Filed: Apr. 5, 2018

(65) Prior Publication Data

US 2018/0230430 A1    Aug. 16, 2018

Related U.S. Application Data

(60) Continuation of application No. 13/419,055, filed on Mar. 13, 2012, now abandoned, which is a division of application No. 11/672,724, filed on Feb. 8, 2007, now Pat. No. 8,158,422.

(60) Provisional application No. 60/743,264, filed on Feb. 9, 2006.

(51) Int. Cl.
*C12N 5/078* (2010.01)

(52) U.S. Cl.
CPC ........ *C12N 5/0641* (2013.01); *C12N 2500/25* (2013.01); *C12N 2501/125* (2013.01); *C12N 2501/14* (2013.01); *C12N 2501/145* (2013.01); *C12N 2501/23* (2013.01); *C12N 2501/39* (2013.01); *C12N 2502/1394* (2013.01); *C12N 2506/02* (2013.01)

(58) Field of Classification Search
CPC .................................................. C12N 5/0641
See application file for complete search history.

(56) References Cited

U.S. PATENT DOCUMENTS 8,158,422 B2    4/2012  Slukvin et al.
2004/0229356 A1  11/2004  Migliaccio et al.

FOREIGN PATENT DOCUMENTS

GB    2449042 A    11/2008
WO    9967360 A2   12/1999

OTHER PUBLICATIONS

Cerdan et al., "VEGF-A165 augments erythropoietic development from human embryonic stem cells", Blood, 103(7), pp. 2504-2512, Apr. 1, 2004 (Jan. 4, 2004).
Examiner's Report dated Feb. 7, 2018, from related Canadian Patent Application No. 2,641,967, 4 pages.
Carotta, et al., Directed Differentiation and Mass Cultivation of Pure Erythroid Progenitors from Mouse Embryonic Stem Cells, Blood, 2004, 104(6):1873-1880.
Kaufman, et al., Hematopoietic Colony Forming Cells Derived from Human Embryonic Stem Cells, PNAS, 2001, 98(19):10716-10721.
Papayannopoulou, et al., Cellular Regulation of Hemoglobin Switching: Evidence for Inverse Relationship Between Fetal Hemoglobin Synthesis and Degree of Maturity of Human Erythroid Cells, Proc. Natl. Acad. Sci. USA, 1979, 76(12):6420-6424.
Qiu, et al., Differentiation of Human Embryonic Stem Cells into Hematopoietic Cells by Coculture with Human Fetal Liver Cells Recapitulates the Globin Switch that Occurs Early in Development, Experimental Hematology, 2005, 33:1450-1458.
Vodyanik, et al., Human Embryonic Stem Cell Derived CD34+ Cells: Efficient Production in the Coculture with OP9 Stromal Cells and Analysis of Lymphohematopoietic Potential, Blood, 2005, 105(2):617-626.
PCT International Search Report, PCT/US2007/003417, dated Oct. 1, 2007.
European Patent Office, Examination Report Application No. 07750270.6, dated Jul. 9, 2010.
Applicant, Response to European Patent Office dated Jul. 9, 2010 Examination Report, Application No. 07750270.6, dated Nov. 4, 2010.
Australian Government IP Australia, Examiners First Report, Application No. 2007215276, dated Dec. 15, 2011.
Applicant, Response to Australian Government IP Australia dated Dec. 15, 2011 Examiner's First Report, Application No. 2007215276, dated Apr. 23, 2012.
Smith, et al., Quantitative PCR Analysis of HbF Inducers in Primary Human Adult Erythroid Cells, Blood, 2000, 95(3):863 869.
Stamatoyannopoulos, et al., Control of Globin Gene Expression During Development and Erythroid Differentiation, Exp. Hematol., 2005, 33(3):259 271.
Steinberg, et al., Disorders of Hemoglobin: Genetics, Pathophysiology, and Clinical Management, Cambridge University Press, 2001.
Canadian Intellectual Property Office, Examiner's Report, Application No. 2,641,967, dated Sep. 25, 2015, 5 pages.
Manor, et al., Improved Method for Diagnosis of Polycythemia Vera Based on Flow Cytometric Analysis of Autonomous Growth of Erythroid Precurors in Liquid Culture, Am. J. Hematol., 1997, 54:47 52, Abstract.
Australian Government IP Australia, Examiners Report No. 2, Application No. 2007215276, dated May 10, 2012.
Wojda et al. Fetal and adult hemoglobin production during adult erythropoiesis: coordinate expression correlates with cell proliferation. Blood, 2002, vol. 99, pp. 3005-3013.
Luo et al Blood, 1999, vol. 94, pp. 359-361.
Duncan et al. J Imanol 1999. vol. 162, pp. 3022-3303.

(Continued)

*Primary Examiner* — Thaian N. Ton
*Assistant Examiner* — David A. Montanari
(74) *Attorney, Agent, or Firm* — Quarles & Brady LLP

(57) ABSTRACT

Methods and compositions of erythroid cells that produce adult β-hemoglobin, generated by culturing CD31+, CD31+/CD34+ or CD34+ cells from embryonic stem cells under serum-free culture conditions.

9 Claims, 3 Drawing Sheets

(56) References Cited

OTHER PUBLICATIONS

Giarratana et al. Ex vivo generation of fully mature human red blood cells from hematopoietic stem cells. Nature Biotechnology, 2005, vol. 23, pp. 69-74.
Chung et al. Human embryonic zeta-globin chains in adult patients with a-thalassemias. PNAS, 1984, vol. 81, pp. 6188-6191.
Tang et al. Human embryonic zeta-globin chain expression in deletional a-thalassemias. Blood, 1992, vol. 80, pp. 517-522.
Chen et al. Comparison of haemoglobin H inclusion bodies with embryonic zeta-globin in screening for a-thalassaemia. J. Clinical Pathology, 1995, vol. 48, pp. 861-864.
Oppenheim et al. Hypomethylation of DNA Derived From Purified Human Erythroid Cells Correlates with Gene Activity of the Beta-Globin Gene Culster. Blood, 1985, vol. 66, pp. 1202-1207.

ERYTHROID CELLS PRODUCING ADULT-TYPE BETA-HEMOGLOBIN GENERATED FROM HUMAN EMBRYONIC STEM CELLS

CROSS-REFERENCE TO RELATED APPLICATIONS

This application is a continuation application of U.S. application Ser. No. 13/419,055 filed Mar. 13, 2012 which was a division of U.S. application Ser. No. 11/672,724 filed Feb. 8, 2007, now U.S. Pat. No. 8,158,422, which claims the benefit of U.S. Provisional Patent Application No. 60/743,264, filed Feb. 9, 2006. All applications are incorporated herein by reference in their entireties.

STATEMENT REGARDING FEDERALLY SPONSORED RESEARCH OR DEVELOPMENT

This invention was made with government support under DAMD17-02-C0130 awarded by the Department of Defense Advanced Research Projects Agency. The government has certain rights in the invention.

BACKGROUND

The present invention relates generally to methods and compositions of erythroid cells generated from human embryonic stem cells (hESCs). More particularly, the present invention relates to methods and compositions of erythroid cells that are at least CD31−, CD34−, CD71+ and CD235a+, and express adult β-hemoglobin and fetal γ-hemoglobin, but not embryonic ζ-hemoglobin.

Hematopoiesis is a formation of blood cell components from stem cells, typically hematopoietic stem cells. Prenatally, hematopoiesis occurs in the yolk sack, then the liver, and eventually the bone marrow. In normal adults, however, it occurs in bone marrow and lymphatic tissues. It has been estimated that there is approximately 1 hematopoietic stem cell per $10^4$ bone marrow cells.

The blood cells produced during hematopoiesis are divided into the following three cell lineages: (1) erythroid cells, (2) lymphoid cells, and (3) myeloid cells. Erythroid cells, including normoblasts, erythroblasts and mature red blood cells (RBCs), are the most common type of blood cell and are a principal means of delivering oxygen from the lungs to body tissues. Lymphoid cells, including B-cells and T-cells, are a type of white blood cell that play a significant role in the body's immune defenses. Myeloid cells, including granulocytes, megakaryocytes, and macrophages, are a diverse group of cells comprising other white blood cells (e.g., neutrophils, eosinophils and basophils) and platelets. Of particular interest herein is the generation of cells of the erythroid lineage.

"Erythropoiesis" is a formation of erythroid cells from stem cells, typically from hematopoietic stem cells. In an average adult, production of mature RBCs (erythrocytes) equals their loss. As such, the average adult produces $3.7 \times 10^{11}$ RBCs/day.

Given the paucity of hematopoietic stem cells, researchers have recently shifted their attention to generating RBCs from embryonic stem cells (ESCs), especially hESCs. hESCs offer an opportunity to generate RBCs in sufficient quantities to study the differentiation of RBCs in vitro. More importantly, RBCs generated from hESCs would provide a safe and an ample alternative source of cells for transfusion, as well as for treating conditions involving defective RBCs (e.g., hypoxia and sickle cell anemia). In the United States, for example, only five percent of eligible donors across the nation donate blood; however, the number of transfusions nationwide increases by nine percent every year.

Recently, Umeda et al. showed that primate ESCs co-cultured with OP9 stromal cells generated cells that expressed embryonic, fetal and adult hemoglobin. Umeda K, et al., "Sequential analysis of alpha- and beta-globin gene expression during erythropoietic differentiation from primate embryonic stem cells," Stem Cells 24:2627-2636 (2006). However, Umeda et al. cultured the cells in serum, which may be problematic due to the uncharacterized composition and variation of serum. Moreover, erythroid cells generated by Umeda et al.'s method contained 5% to 15% myeloid cells.

Likewise, Olivier et al. showed that hESCs co-cultured with human fetal liver cells generated CD34+ cells that produced embryonic and fetal hemoglobin. Olivier E, et al., "Large-scale production of embryonic red blood cells from human embryonic stem cells," Exp. Hematol. 34:1635-1642 (2006); for similar results, see also Qiu C., et al., "Differentiation of human embryonic stem cells into hematopoietic cells by coculture with human fetal liver cells recapitulates the globin switch that occurs early in development," Exp. Hematol. 33:1450-1458 (2005). Unfortunately, Olivier et al.'s cells did not produce adult hemoglobin and retained expression of embryonic ζ-hemoglobin.

Other researchers have also generated RBCs from ESCs; however, these methods either used non-human/non-primate stem cells or used an embryoid body-dependent method (i.e. no direct differentiation). These methods, however, produced a mixture of erythroid and myeloid cells. See Carotta S, et al., "Directed differentiation and mass cultivation of pure erythroid progenitors from mouse embryonic stem cells," Blood 104:1873-1880 (2004); Chadwick K, et al., "Cytokines and BMP-4 promote hematopoietic differentiation of human embryonic stem cells," Blood 102:906-915 (2003); Kaufman D, et al., "Hematopoietic colony-forming cells derived from human embryonic stem cells," Proc. Natl. Acad. Sci. USA 98:10716-10721 (2001); Ng, E, et al., "Forced aggregation of defined numbers of human embryonic stem cells into embryoid bodies fosters robust, reproducible hematopoietic differentiation," Blood 106:1601-1603 (2005); and Zambidis E, et al., "Hematopoietic differentiation of human embryonic stem cells progresses through sequential hematoendothelial, primitive, and definitive stages resembling human yolk sac development," Blood 106:860-870 (2005).

For the foregoing reasons, there is a continuing need for alternative methods of generating erythroid cells from hESCs, especially erythroid cells that express adult hemoglobin, that are generated under plasma/serum-free conditions and that are free of lymphocytes.

BRIEF SUMMARY

In a first aspect, a method of culturing human embryonic stem cells into erythroid cells producing adult-type β-hemoglobin includes isolating human embryonic stem cell-derived cells that are CD31+, CD34+, and CD31+/CD34+ cells, such that the cells are enriched in CD31+/CD43+, CD31+/CD34+, CD34+/CD43+ or CD31+/CD34+/CD43+ hematopoietic progenitors. The method also includes culturing the hematopoietic progenitors to cause an expansion of erythroid precursor cells. The method further includes recovering a population of erythroid cells, such that essentially all of the live cells are erythroid cells that produce adult β-hemoglobin, but not embryonic ζ-hemoglobin.

In some embodiments of the first aspect, the population of erythroid cells are essentially free of lymphocytes. In other embodiments of the first aspect, the erythroid cells contain less than 0.1% leukocytes.

In some embodiments of the first aspect, the hematopoietic progenitors are cultured in the presence of stem cell factor and erythropoietin under conditions preventing cell adherence.

In some embodiments of the first aspect, the human embryonic stem cells are co-cultured with stromal cells to produce the hematopoietic progenitors.

In some embodiments of the first aspect, at least $0.2 \times 10^5$ erythroid cells are generated from one human embryonic stem cell. In other embodiments of the first aspect, up to $2.0 \times 10^5$ erythroid cells are generated from one human embryonic stem cell.

In some embodiments of the first aspect, the erythroid cells produce adult-type β-hemoglobin, are CD31−, CD34−, CD71+, CD235a+ and additionally express fetal γ-hemoglobin. In other embodiments of the first aspect, the erythroid cells do not express embryonic ζ-hemoglobin.

In some embodiments of the first aspect, the purity of the isolated hematopoietic progenitors are greater than 95% at a single column run and cell viability, as evaluated by Trypan blue exclusion, is higher than 95%.

In some embodiments of the first aspect, the CD31+/CD34+ cells comprise 30% to 50% CD31+/CD34+/CD43+ hematopoietic progenitors and 50% to 70% CD31+/CD34+/CD43−/KDR$^{bright}$ endothelial cells.

In some embodiments of the first aspect, the cells express adult β-hemoglobin by 10 days (±10%) of culture, and most of the cells have a phenotype and a morphology of erythroid cells.

In some embodiments of the first aspect, after approximately 30 days (±10%) of culture, essentially all of the live erythroid cells (>95%) show positive stains with antibodies against fetal γ-hemoglobin and adult β-hemoglobin, but no positive staining with antibodies against embryonic ζ-hemoglobin. In other embodiments of the first aspect, after approximately 50 days (±10%) of culture, the erythroid cells are CD31−/CD34− and show adult β-hemoglobin expression and no embryonic ζ-hemoglobin expression.

In some embodiments of the first aspect, the hematopoietic precursors are cultured in serum-free culture conditions.

In a second aspect, a cell population includes a population of cells, such that essentially all of the live cells are erythroid cells that produce adult β-hemoglobin, but not embryonic ζ-hemoglobin.

In some embodiments of the second aspect, the population of essentially all live cells are nucleated erythroid cells. In other embodiments of the second aspect, the population is essentially free of lymphocytes. In further embodiments of the second aspect, the population contains less than 0.1% leukocytes. In alternative embodiments of the second aspect, the population is CD31−, CD34−, CD71+ and CD235a+.

In a third aspect, a preparation of cells includes CD31+/CD34+/CD43+ hematopoietic progenitor cells.

In some embodiments of the third aspect, the preparation of cells are a result of 6 to 7 days (±10%) co-culture between human embryonic stem cells and OP9 cells.

In a fourth aspect, a CD31+ cell population includes 10% to 20% CD31+/CD43+ hematopoietic progenitors, up to 60% CD34+/CD43−/KDR$^{bright}$ endothelial cells and less than 15% CD34+/CD43−/KDR− mesenchymal cells.

In a fifth aspect, a CD34+ cell population includes 10% to 20% CD34+/CD43+ hematopoietic progenitors, up to 60% CD34+/CD43−/KDR$^{bright}$ endothelial cells and less than 15% CD34+/CD43−/KDR− mesenchymal cells.

BRIEF DESCRIPTION OF DRAWINGS

The invention will be better understood and features, aspects and advantages other than those set forth above will become apparent when consideration is given to the following detailed description thereof. Such detailed description makes reference to the following drawings, wherein.

Figure 1:
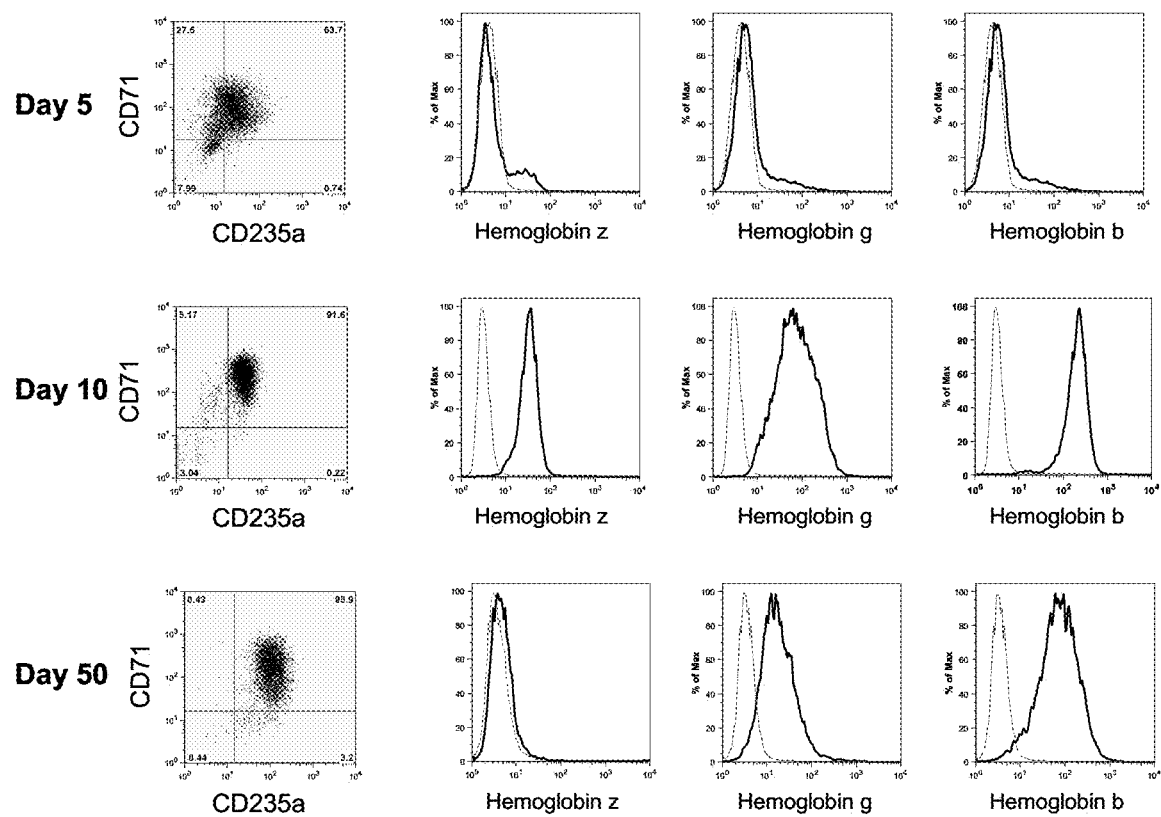
FIG. 1 shows results from flow cytometric analysis of hESC-derived erythroid cells at differentiation day 5, 10 and 50 of culture.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

BRIEF DESCRIPTION OF THE INVENTION

In one embodiment, the present invention is a generation of a cell population of erythroid cells producing adult-type β-hemoglobin from hESCs. By "erythroid cells producing adult-type β-hemoglobin," we mean cells that are CD31−, CD34−, CD71+, CD235a+ and that express adult β-hemoglobin and fetal γ-hemoglobin, but not embryonic ζ-hemoglobin, as determined by PCR and flow cytometry using hemoglobin-specific antibodies. Morphologically, the cell population consists of nucleated erythroid cells at different stages of maturation, including, but not limited to, normoblasts and erythroblasts. The population contains less then 0.1% leukocytes as determined by staining with anti-CD45 monoclonal antibodies and is essentially free of lymphocytes. By "essentially free of lymphocytes," we mean that the lymphoid cells cannot be detected using flow cytometry with monoclonal antibodies against B-cells (CD19), T-cells (CD3) and NK cells (CD94), or by RT-PCR through amplification of B-cell (V-preB), T-cell (pre-Tα) and NK cell (CD94) specific transcripts.

It is an advantage that the hESC-derived erythroid cells, if prepared by the methods described herein, have not been exposed to blood plasma or serum. In a preferred embodiment, the cells of the present invention are "plasma free" and have never been exposed to human, or any other type, of blood plasma or serum.

It is also an advantage that the hESC-derived erythroid cells produced by the methods described herein can be used to produce younger cells (i.e. normoblasts and erythroblasts) that have prolonged survival. This trait would be beneficial for patients who require multiple transfusions, for example chronic anemia patients.

It is also an advantage that the hESC-derived erythroid cells produced by the methods described herein express adult hemoglobin following co-culture (i.e. after selection of CD31+ and/or CD34+ hematopoietic progenitor cells).

It is also an advantage that the hESC-derived erythroid cells can be produced by the methods described herein free of viruses to reduce the risk of CMV, HTLV-I/II and prion (Creutzfeldt-Jakob disease, and new variant Creutzfeldt-Jakob disease) transmission.

It is also an advantage that the hESC-derived erythroid cells are free of lymphocytes. This is beneficial for use in immunosuppressed individuals who are at increased risk of developing graft-versus-host reaction after transfusion.

It is also an advantage that at least $0.2 \times 10^5$ to preferably $2.0 \times 10^5$ erythroid cells are generated from one human embryonic stem cell.

We had previously isolated different types of hematopoietic precursors from hESC/OP9 co-culture: CD31+, CD34+, CD235a+, CD43+lin− and CD45+lin− cells. Vodyanik M, et al., "Human embryonic stem cell-derived CD34+ cells: efficient production in the coculture with OP9 stromal cells and analysis of lymphohematopoietic potential," Blood 105: 617-626 (2005); see also Vodyanik M, et al., "Leukosialin (CD43) defines hematopoietic progenitors in human embryonic stem cell differentiation cultures. Blood 108:2095-2105 (2006), each of which is incorporated herein by reference as if set forth in its entirety. All of these hematopoietic precursor cells can be directly differentiated into RBCs; however, the best expansion of erythroid cells was achieved when we used hESC-derived CD31+ or CD34+ hematopoietic progenitors as described below.

Several publications describe differentiation of ESCs into a mixture of hematopoietic cells (Chadwick et al., supra; Ng et al., supra; and Zambidis et al., supra), but there is no description of directed differentiation of hESCs to erythroid cells that are at least CD31−, CD34−, CD71+ and CD235a+ and that express adult β-hemoglobin. Other work has described directed differentiation of mouse ESCs (Carotta et al., supra) and human somatic CD34+ cells into RBCs. Giarratana M, et al., "Ex vivo generation of fully mature human red blood cells from hematopoietic stem cells," Nat. Biotechnol. 23:69-74 (2005).

Recent work describes differentiation of hESCs into hematopoietic cells containing RBCs using a bone marrow stromal cell line (S17) and a human fetal liver-derived cell line (FH-B-hTERT). However, RBCs obtained in these systems produced embryonic ε-hemoglobin and fetal γ- and ζ-hemoglobin, but failed to express adult β-hemoglobin (Qiu et al., supra).

Figure 3:
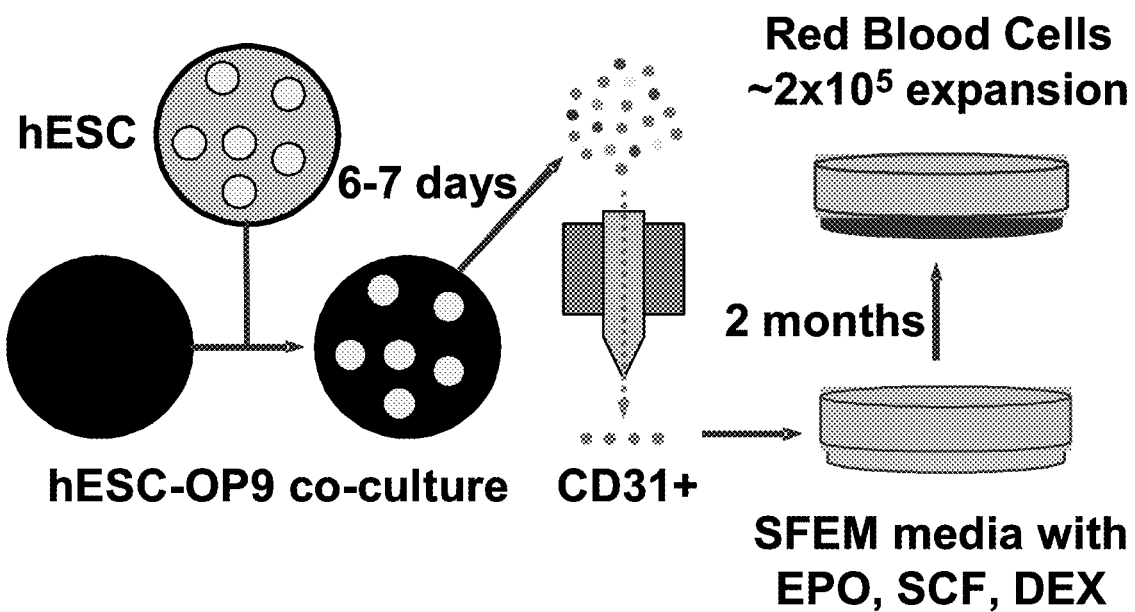
FIG. 3 shows a diagram that summarizes one embodiment of the generation of hESC-derived erythroid cells.

In one embodiment of the present invention, erythroid cells are obtained by the following method (see FIG. 3):

One preferably first differentiates hESCs into CD31+ and/or CD34+ cells. We have used H1 and H9 hESCs (WiCell; Madison, Wis.) for the examples described below, but any hESC line is suitable. The best expansion was achieved when we used CD34+ cells that comprised 10% to 20% of CD34+/CD43+ hematopoietic progenitors, and up to 60% of CD34+/CD43−/KDR$^{bright}$ endothelial cells and less than 15% of CD34+/CD43−/KDR− mesenchymal cells, or CD31+ cells that comprised 30% to 50% CD31+/CD34+/CD43+ hematopoietic progenitors, and up to 50% to 70% CD31+/CD34+/CD43−/KDR$^{bright}$ endothelial cells.

Preferably, one begins by co-culturing hESCs with a stromal cell line, such as mouse OP9 bone marrow stromal cells. In addition, the stromal cell line should not express macrophage colony stimulating factor. Other bone marrow stromal lines are suitable as long as the line results in efficient production of CD31+, CD31+/CD34+ or CD34+ hematopoietic progenitors.

By "efficient," we mean that at least 5% to 10% CD31+ and/or CD34+ cells are generated and that these cells comprise at least 30% to 50% CD31+/CD34+/CD43+ hematopoietic progenitors, and up to 70% CD31+/CD34+/KDR$^{bright}$/CD43− endothelial cells.

ESC differentiation into hematopoietic progenitors has been described by us and others. Vodyanik et al., supra; and Kaufman et al., supra. One could also obtain hematopoietic progenitors from embryoid bodies (see, e.g., Chadwick et al., supra; Zambidis et al., supra; and Ng et al., supra.).

Preferably, the hESCs are added to OP9 cultures at a density of $1.5 \times 10^6/20$ ml ($\pm 10\%$) per 10 cm dish, in α-MEM (minimal essential media; GIBCO) supplemented with 10% fetal bovine serum (FBS; HyClone; Logan, Utah) and 100 µM monothioglycerol (MTG; Sigma; St. Louis, Mo.). The example below describes a preferable density of the hESCs.

The hESC/OP9 co-cultures are incubated for up to 10 days at 37° C. in normoxic conditions and 5% $CO_2$, with a half-medium change on day 4. A single-cell suspension is prepared on day 6 of culture. The cells are harvested and single cell suspensions are prepared by treatment of the co-culture with collagenase IV, typically at 1 mg/ml ($\pm 10\%$) in α-MEM for 20 minutes at 37° C. followed by treatment with 0.05% trypsin-0.5 mM EDTA (Invitrogen) for 15 minutes at 37° C.

At this point, one would typically have a single cell suspension of cells that contains at least 5% to 10% CD31+ cells, preferably as measured by anti-CD31 monoclonal antibodies. For example, in a typical isolation of CD31+ cells using paramagnetic antibodies, the purity of the isolated CD31+ cells is greater than 95% at a single column run and cell viability, as evaluated by Trypan blue exclusion, is typically higher than 95%. By "single column run," we mean a single round of cell purification using magnetic beads. Likewise, cells could be assayed with anti-CD34 monoclonal antibodies.

The conditions described herein provide the best hematopoietic differentiation (hematopoietic cell output) of which we are aware. We know from previous studies (Vodyanik et al., supra) that by day 7 we get the highest number of erythroid progenitors in OP9 co-culture, including definitive erythroid progenitors as determined using colony-forming assay followed by analysis of hemoglobin expression in colonies by PCR.

To expand and differentiate the erythroid cells, CD31+ and/or CD34+ cells are typically cultured in serum-free expansion media (SFEM medium; Stem Cell Technologies; Vancouver, Canada) supplemented with, preferably, 0.3% ($\pm 10\%$) EX-CYTE® (Serologicals Proteins, Inc.; Kankakee, Ill.), 1 mg/ml ($\pm 20\%$) iron-saturated transferrin (Sigma), $10^{-6}$ M ($\pm 10\%$) dexamethasone, and 20 ng/ml ($\pm 10\%$) insulin in tissue culture flasks coated with a substance to prevent cell adherence, such as poly 2-hydroxyethyl methacrylate (HEMA; Sigma). For the first 5 days, cells are typically cultured in the presence of 50 ng/ml ($\pm 10\%$) stem cell factor (SCF), 2 U/ml ($\pm 10\%$) erythropoietin (EPO), 50 ng/ml ($\pm 10\%$) thrombopoietin (TPO), 5 ng/ml ($\pm 10\%$) IL-3 and 10 ng/ml ($\pm 10\%$) IL-6. After 6 days, cells are expanded in the same medium without TPO, IL-3 and IL-6.

Alternatively, differentiation and expansion of erythroid cells can be performed on a stromal cell line such as MS-5, using the same medium and cytokine combinations. This culture condition resulted in a generation of a higher percentage of more mature erythroid cells such as normoblasts when compared to feeder-free conditions.

As described below, cell differentiation is preferably monitored by morphological analysis of cytospins (i.e. cells were spun onto glass slides using a centrifuge so that cells can be stained and evaluated morphologically) and flow cytometry using anti-CD71 and anti-CD235a antibodies. Also as described below, one can analyze cell hemoglobin content, preferably by flow cytometry using indirect staining with antibodies against human embryonic hemoglobin, fetal hemoglobin and adult hemoglobin and by PCR using embryonic, fetal and adult hemoglobin-specific primers.

After 5 days (±10%) of culture, the majority of live cells are erythroid precursors and express CD71 and CD235a. After 10 days (±10%) of culture, most of the cells have a phenotype and a morphology of erythroid cells. By PCR, erythroid cells express high level of embryonic ζ- and fetal γ-hemoglobin, and low level of adult β-hemoglobin, as determined by PCR. After approximately 30 days of culture (±10%), essentially all of the live cells (>95%) show positive stains with antibodies against fetal and adult hemoglobin, but no positive staining with antibodies against embryonic ζ-hemoglobin. Following expansion, β-hemoglobin expression increased and ζ-hemoglobin expression decreased, and eventually disappeared by day 50 of culture, preferably as determined by PCR. The cells are CD31− and CD34−. At this point, the cells are "erythroid cells producing adult-type β-hemoglobin" of the present invention.

With respect to CD31+ cells, Vodyanik et al. describes an early CD31+/CD34+/CD43+ hematopoietic progenitor and other CD34+ cell populations derived from hESC differentiation and embodies methods and CD34+ cell populations that are part of the present invention. Vodyanik M, et al., "Leukosialin (CD43) defines hematopoietic progenitors in human embryonic stem cell differentiation cultures," Blood 108:2095-2105 (2006), incorporated herein by reference as if set forth in its entirety.

EXAMPLES

Example 1: Differentiation of hESCs into CD31+ Cells and/or CD34+

Differentiation of hESCs into CD31+ and/or CD34+ cells was achieved by co-culture of hESCs with a mouse OP9 bone marrow stromal cell line.

Undifferentiated hESCs (H1 and H9 lines; WiCell; Madison, Wis.) were harvested by treatment with 1 mg/ml collagenase IV (Invitrogen) and dispersed by scraping to maintain the cells in small clumps. The hESCs were added to OP9 bone marrow stromal cells obtained from Dr. Toru Nakano (Research Institute for Microbial Diseases, Osaka University, Japan, also available from ATCC) at a hESC density of $1.5 \times 10^6/20$ ml per 10 cm dish, or $0.3 \times 10^6/4$ ml per well of a 6-well plate, in α-MEM supplemented with 10% FBS (HyClone) and 100 μM MTG (Sigma).

The hESC/OP9 co-cultures were incubated for 6-7 days at 37° C. in normoxic conditions and 5% $CO_2$ with a half-medium change on day 4. On day 6-7, cells were harvested and a single-cell suspension was prepared by treatment of the hESC/OP9 co-cultures with collagenase IV (Invitrogen; 1 mg/ml in α-MEM) for 20 minutes at 37° C. followed by treatment with 0.05% trypsin-0.5 mM EDTA (Invitrogen) for 15 minutes at 37° C.

The single-cell suspension was labeled with CD31 paramagnetic monoclonal antibodies using Direct CD31 Microbead Kit (Miltenyi Biotech; Auburn, Calif.) as recommended by the manufacturer, and processed through an LS+ separation column attached to a Midi-MACS separation unit (Miltenyi Biotech) to obtain the magnet-retained fraction of purified cells. Alternatively, or in addition, the single-cell suspension was labeled with CD34 paramagnetic monoclonal antibodies (Miltenyi Biotech). Purity of isolated CD31+ and/or CD34+ cells, as determined by flow cytometry, was generally greater than 95% at a single column run, and cell viability, as evaluated by Trypan blue exclusion, was always higher than 95%.

Example 2: Large-Scale Expansion of Human Erythroid Progenitor Cells

To expand erythroid cells, CD31+ and/or CD34+ cells were cultured in SFEM (Stem Cell Technologies) supplemented with 0.3% of EX-CYTE (Serologicals Proteins, Inc.), 1 mg/ml iron saturated transferrin (Sigma), $10^{-6}$ M dexamethasone, and 20 ng/ml insulin in tissue culture flasks coated with HEMA to prevent cell adherence. For the first 5 days, cells were cultured in the presence of 50 ng/ml SCF, 2 U/ml EPO, 50 ng/ml TPO, 5 ng/ml IL-3 and 10 ng/ml IL-6. The subsequent incubations were performed in the same media with insulin, transferrin, dexamethasone, SCF and EPO only, with medium changed every second day.

Cell differentiation was monitored throughout culture by morphological analysis of cytospins and by flow cytometry using anti-CD71 (transferrin receptor) and anti-CD235a (Glycophorin A) monoclonal antibodies. Hemoglobin analysis was performed by flow cytometry on cells permeabilized with FIX&PERM® cell permeabilization reagent (Caltag; Burlingame, Calif.) using indirect staining with antibodies against human embryonic hemoglobin ζ, fetal hemoglobin γ and adult hemoglobin β chains (Perkin Elmer; Norton, Ohio). In addition, hemoglobin expression was evaluated using PCR with primers specific for ζ-, γ- and β-hemoglobin.

β-hemoglobin is adult hemoglobin. ζ-hemoglobin is embryonic and present only during embryonic development. γ-hemoglobin is usually present during the neonatal period and can be found in some conditions in adults. The presence of β-hemoglobin indicates that the erythroid cells are not embryonic, as embryonic cells are β-hemoglobin negative.

Figure 2:
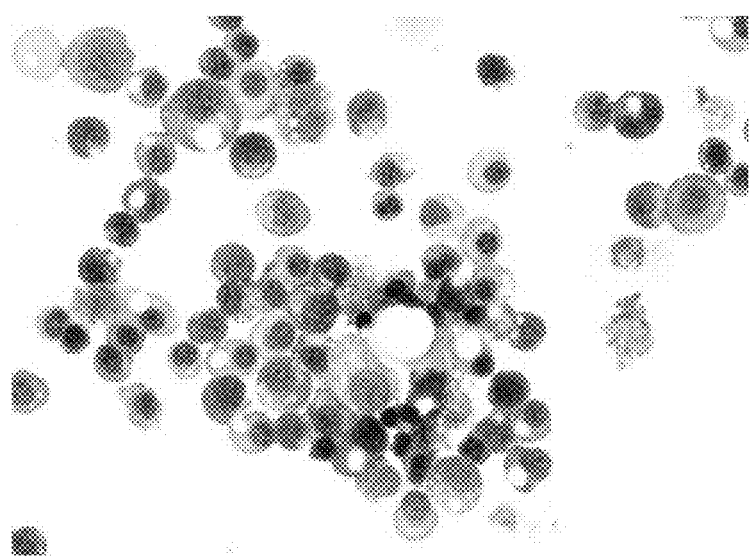
FIG. 2 shows morphology of erythroid precursors generated from hESC-derived CD34+ progenitors after two weeks of culture.

After 5 days of culture, the majority of the cells were erythroid precursors and expressed CD71 and CD235a (glycophorin). However, only a few cells were positive for hemoglobins. During next 5 days (day 10 of culture), essentially all of the live cells in culture (>95%) had phenotype and morphology of erythroid cells (CD71+/CD235a+) (FIGS. 1 and 2). All cells contain embryonic (ζ) and adult (β) hemoglobins as determined by flow cytometry (FIG. 1) and by PCR.

After 50 days of culture, we observed at least a $2 \times 10^5$ expansion of erythroid cells, and all erythroid cells showed positive stains with antibodies against fetal (γ) and adult (β) hemoglobin, but no positive staining detected with antibodies against embryonic (ζ) hemoglobin (see FIG. 1). By PCR, cells expressed adult β-hemoglobin and fetal γ-hemoglobin, but not embryonic ζ-hemoglobin. Morphologically, the cell population consisted of nucleated erythroid cells at different states of maturation, including erythroblasts and normoblasts (FIG. 2). The hESC-derived erythroid cells contained less than 0.1% of leukocytes as determined by staining with anti-CD45 monoclonal antibodies and were "essentially free of lymphocytes," as determined by flow cytometry and RT-PCR for lymphoid markers.

Erythroid cells proliferated in culture for up to 60 days. After 60 days the cells stop proliferating and eventually died.

We claim:

1. A method of making a blood product for use in transfusions, the method comprising:
   (a) culturing human embryonic stem cells under conditions which favor differentiation of the cells into hematopoietic progenitors;
   (b) isolating cells from step (a) selected from the group consisting of CD31+, CD34+, and CD31+/CD34+ cells, wherein the cells are enriched in CD31+/CD43+, CD31+/CD34+, CD34+/CD43+ or CD31+/CD34+/CD43+ hematopoietic progenitors;
   (c) culturing in serum free conditions the isolated CD31+, CD31+/CD34+ and CD34+ cells to cause differentiation to erythroid precursor cells, and
   (d) self-renewal/expansion and maturation of the erythroid precursor cells to produce a pure population of human erythroid cells, wherein the population of human erythroid cells is CD71+ and produces adult β-hemoglobin and fetal γ-hemoglobin but not embryonic ζ-hemoglobin,
   wherein the blood product comprises the isolated human erythroid cells of step (d) and is essentially free of lymphocytes.

2. The method of claim 1, wherein the blood product does not contain serum.

3. The method of claim 1, wherein the blood product contains less than 0.1% leukocytes.

4. The method of claim 1, wherein the culturing of step (c) is in the presence of stem cell factor and erythropoietin under conditions preventing cell adherence.

5. The method of claim 1, wherein the human embryonic stem cells are co-cultured with stromal cells to produce the hematopoietic progenitors.

6. The method of claim 1, wherein at least $0.2 \times 10^5$ erythroid cells are generated from one human embryonic stem cell.

7. The method of claim 1, wherein the cells of step (d), which produce adult-type β-hemoglobin, are CD31−, CD34−, CD71+, CD235a+.

8. The method of claim 1, wherein the blood product comprises at least 95% live cells that stain positive with antibodies against fetal γ-hemoglobin and adult β-hemoglobin, but do not stain positive with antibodies against embryonic ζ-hemoglobin.

9. The method of claim 8, wherein the live cells are nucleated erythroid cells.

* * * * *